United States Patent
Forsell (10) Patent No.: US 9,968,482 B2
(45) Date of Patent: May 15, 2018

(54) SYSTEM AND METHOD FOR THERMAL TREATMENT OF HYPERTENSION, HYPOTENSION OR ANEURYSM

(76) Inventor: Peter Forsell, Zug (CH)

( * ) Notice: Subject to any disclaimer, the term of this patent is extended or adjusted under 35 U.S.C. 154(b) by 882 days.

(21) Appl. No.: 12/682,334

(22) PCT Filed: Oct. 10, 2008

(86) PCT No.: PCT/SE2008/000581
§ 371 (c)(1),
(2), (4) Date: Apr. 9, 2010

(87) PCT Pub. No.: WO2009/048390
PCT Pub. Date: Apr. 16, 2009

(65) Prior Publication Data
US 2010/0217295 A1  Aug. 26, 2010

Related U.S. Application Data (60) Provisional application No. 60/960,715, filed on Oct. 11, 2007, provisional application No. 60/960,716, (Continued)

(51) Int. Cl.
*A61F 7/12* (2006.01)
*A61B 17/12* (2006.01)
(Continued)

(52) U.S. Cl.
CPC ............... *A61F 7/12* (2013.01); *A61B 17/12* (2013.01); *A61B 90/361* (2016.02); *A61F 7/007* (2013.01);
(Continued)

(58) Field of Classification Search
USPC .................. 607/96–114, 44; 623/1.1–3.3
See application file for complete search history.

(56) References Cited

U.S. PATENT DOCUMENTS 5,759,199 A * 6/1998 Snell et al. ..................... 607/60
6,048,333 A   4/2000 Lennox et al.
(Continued)

FOREIGN PATENT DOCUMENTS

WO         00/64387    11/2000
WO    WO 2002/005736    1/2002
(Continued)

OTHER PUBLICATIONS

U.S. Appl. No. 12/682,462 (Forsell) filed Apr. 9, 2010.
(Continued)

*Primary Examiner* — Joseph Stoklosa
*Assistant Examiner* — Adam Avigan (57) ABSTRACT

In accordance with the present invention, there is provided a system for treating a patient with local hypertension, comprising a hypertension treatment device adapted to have at least one surface of the device attached to the blood flow passageway, wherein said surface comprising a cooling surface able to cool said passageway to restrict said passageway thereby reducing the blood pressure distal to said restriction. In accordance with a another aspect of the present invention, there is provided a system for treating a patient with aneurysm, comprising a aneurysm treatment device adapted to have at least one surface of the device attached to the blood flow passageway, wherein said surface comprising a cooling surface able to cool said passageway to restrict said passageway thereby treating said aneurysm. In accordance with a second aspect of the present invention, there is provided a system for treating a patient with hypotension, comprising a hypotension treatment device adapted to have at least one surface of the device attached to the blood flow passageway, wherein said surface comprising a heating surface able to heat said passageway to dilate said (Continued)

passageway thereby increasing the blood pressure distal to said restriction.

20 Claims, 9 Drawing Sheets

Related U.S. Application Data filed on Oct. 11, 2007, provisional application No. 61/000,733, filed on Oct. 29, 2007.

(51) Int. Cl.
*A61F 7/00* (2006.01)
*A61B 90/00* (2016.01)

(52) U.S. Cl.
CPC .............. *A61F 2007/0075* (2013.01); *A61F 2007/0094* (2013.01)

(56) References Cited

U.S. PATENT DOCUMENTS

| | | | |
|---|---|---|---|
| 6,428,563 B1 | 8/2002 | Keller | |
| 6,942,686 B1 | 9/2005 | Barbut et al. | |
| 7,617,005 B2 * | 11/2009 | Demarais et al. | 607/116 |
| 8,150,518 B2 * | 4/2012 | Levin et al. | 607/44 |
| 8,828,068 B2 * | 9/2014 | Arcot-Krishnamurthy et al. | 607/113 |
| 2003/0060814 A1 | 3/2003 | Capuano et al. | |
| 2004/0220521 A1 | 11/2004 | Barbut | |
| 2005/0222649 A1 | 10/2005 | Capuano et al. | |
| 2005/0266042 A1 | 12/2005 | Tseng | |
| 2006/0253193 A1 | 11/2006 | Lichtenstein et al. | |
| 2007/0038259 A1 | 2/2007 | Kieval et al. | |
| 2007/0225781 A1 * | 9/2007 | Saadat et al. | 607/105 |
| 2010/0210955 A1 | 8/2010 | Forsell | |
| 2010/0211091 A1 | 8/2010 | Forsell | |
| 2010/0211092 A1 | 8/2010 | Forsell | |
| 2011/0066254 A1 | 3/2011 | Forsell | |
| 2011/0087337 A1 | 4/2011 | Forsell | |

FOREIGN PATENT DOCUMENTS

| | | |
|---|---|---|
| WO | 2004/026112 | 4/2004 |
| WO | 2005/084730 | 9/2005 |
| WO | 2006/037088 | 4/2006 |
| WO | 2006/039555 | 4/2006 |
| WO | WO 2009/011738 | 1/2009 |

OTHER PUBLICATIONS

U.S. Appl. No. 12/682,501 (Forsell) filed Apr. 9, 2010.
U.S. Appl. No. 12/682,491 (Forsell) filed Apr. 9, 2010.
U.S. Appl. No. 12/758,684 (Forsell) filed Apr. 12, 2010.
U.S. Appl. No. 12/758,694 (Forsell) filed Apr. 12, 2010.
International Search Report for PCT/SE2008/000581, dated Feb. 5, 2009.
Patent Examination Report No. 1, Australian Patent Application No. 2008311443, dated May 27, 2013.

\* cited by examiner

SYSTEM AND METHOD FOR THERMAL TREATMENT OF HYPERTENSION, HYPOTENSION OR ANEURYSM

This application is the U.S. national phase of International Application Nos. PCT/SE2008/000581, filed 10 Oct. 2008, which designated the U.S. and claims priority to U.S. Application Nos. 60/960,715, filed 11 Oct. 2007, 60/960, 716, filed 11 Oct. 2007 and 61/000,733, filed 29 Oct. 2007, the entire contents of each of which are hereby incorporated by reference.

FIELD OF THE INVENTION

The present invention relates generally to medical devices and treatment and, more particularly, to a system and a method for treatment of hypertension or hypotension in a local part of the vascular system of a patient.

BACKGROUND OF THE INVENTION

Hypertension, commonly referred to as "high blood pressure" or HTN, is a medical condition in which the blood pressure is chronically elevated. Hypertension may occur when the body's smaller blood vessels (arterioles) constrict, causing an increase in blood pressure. Because the blood vessels constrict, the heart must work harder to maintain blood flow at the higher pressures. Although the body may tolerate short periods of increased blood pressure, sustained hypertension may eventually result in damage to multiple body organs, including the kidneys, brain, eyes and other tissues, causing a variety of maladies associated therewith. The elevated blood pressure may also damage the lining of the blood vessels, accelerating the process of atherosclerosis and increasing the likelihood that a blood clot may develop. This could lead to a heart attack and/or stroke. Sustained high blood pressure may eventually result in an enlarged and damaged heart (hypertrophy), which may lead to heart failure.

Hypotension, on the other hand, refers to an abnormally low blood pressure. This is best understood as a physiologic state, rather than a disease. It is often associated with shock, though not necessarily indicative of it.

Hypertension or hypotension is not something that only affects the whole vascular system, sometimes it is a local part of the vascular system that is affected. By locally dilate or constrict the blood vessel creating the local problem of hypo- or hypertension this problem could be treated. To avoid any kind of damage to the blood vessel a system using heat or cold could be used to regulate the constriction or dilatation of the blood vessel.

Hypertension may occur in the pulmonary system with too high blood pressure in the pulmonary artery. This could be caused by defective heart valves but often the cause is unknown.

Hypotension may occur in the renal artery only causing general hypertension because regulation factors are produced in the kidney, which wrongly detects that hypotension is on hand.

BRIEF SUMMARY OF THE INVENTION

An object of the present invention is to provide a system and a method for treatment of hypertension or hypotension in a local part of the vascular system of a patient.

A constriction device placed on the pulmonary artery of a patient with high blood pressure, either one device before or two devices after the bifurcation, may treat the hypertension locally in the vascular pulmonary system. To avoid damaging the blood vessel the system is adapted to use a cooling surface to achieve the constriction.

Another important example is hypotension in the renal artery only causing general hypertension because regulation factors are produced in the kidney, which feels that hypotension is on hand. Locally treating the hypotension could be achieved by heating the renal artery causing dilatation thereof.

Another way of causing contraction may be to combine the cooling system with a stimulation device to stimulate the blood vessel with electrical pulses. Electric stimulation has been proposed to treat aneurysm to strengthen the wall of the blood vessel by increasing the tonus therein. However, we believe electric stimulation in combination with thermal stimulation may also be used also to treat local hypertension as well as aneurysm.

In accordance with a first aspect of the present invention, there is provided a system for treating a patient with hypertension, comprising a hypertension treatment device adapted to have at least one surface of the device attached to the blood flow passageway, wherein said surface comprising a cooling surface able to cool said passageway to restrict said passageway thereby reducing the blood pressure distal to said restriction.

In a preferred embodiment, the system comprises a control device for controlling the temperature of the cooling surface. A sensor preferably senses a physical parameter of the patient, preferably the blood pressure, or a functional parameter of the device, wherein the internal control unit controls said cooling surface in response to said sensor.

In a preferred embodiment, the system comprises a mechanical or hydraulic constriction device for co-operating with said cooling surface to cause said restriction.

In a preferred embodiment, the system comprises an internal control unit, wherein the temperature of the cooling surface is controlled by the internal control unit.

In one embodiment the hypertension treatment device is adapted to be placed on the pulmonary artery to reduce high blood pressure in the pulmonary region. In a preferred embodiment, the system comprises a power supply, preferably a rechargeable power supply, and an electronic circuitry adapted to power the cooling surface.

In a preferred embodiment, the cooling surface comprising an electronic element, preferably a peltier element, further creating heat on a second surface. A cooling system easiest using water may be adapted to transport away heat from the second surface.

In accordance with a second aspect of the present invention, there is provided a system for treating a patient with hypotension, comprising a hypotension treatment device adapted to have at least one surface of the device attached to the blood flow passageway, wherein said surface comprising a heating surface able to heat said passageway to dilate said passageway thereby increasing the blood pressure distal to said restriction.

In a preferred embodiment, the system comprises a control device for controlling the temperature of the heating surface. A sensor preferably senses a physical parameter of the patient, preferably the blood pressure, or a functional parameter of the device, wherein the internal control unit controls said heating surface in response to said sensor.

In a preferred embodiment, the system comprises a mechanical or hydraulic constriction device for co-operating with said heating surface to cause said restriction.

In a preferred embodiment, the system comprises an internal control unit, wherein the temperature of the heating surface is controlled by the internal control unit.

In a preferred embodiment, the hypotension treatment device is adapted to be placed on the renal artery to increase the blood pressure in the renal region.

In a preferred embodiment, the system comprises a power supply, preferably a rechargeable power supply, and an electronic circuitry adapted to power the heating surface.

In a preferred embodiment, the heating surface comprising an electronic element, preferably a peltier element, further creating cold on a second surface. A heating system easiest using water may be adapted to transport away cold from the second surface.

In accordance with a third aspect of the present invention, there is provided a system for treating a patient with aneurysm, comprising a aneurysm treatment device adapted to have at least one surface of the device attached to an aneurysm in the blood flow passageway, wherein said surface comprising a cooling surface able to cool said passageway to a) reduce the dilatation of said dilated aneurysmatic passageway or b) increase the tonus of said dilated aneurysmatic passageway thereby reducing the risk of further dilatation of said aneurysm.

In a preferred embodiment, the aneurysm treatment device, comprising a control device for controlling the temperature of said cooling surface.

In a preferred embodiment, the aneurysm treatment device, comprising a mechanical or hydraulic constriction device for co-operating with said cooling surface to cause said restriction.

In a preferred embodiment, the aneurysm treatment device, comprising an internal control unit, wherein the temperature of said cooling surface is controlled by the internal control unit.

In a preferred embodiment, the aneurysm treatment device, comprising a sensor sensing a physical parameter of the patient or a functional parameter of the device, wherein the internal control unit controls said cooling surface in response to said sensor.

In a preferred embodiment, said sensor is sensing the blood pressure.

In a preferred embodiment, said aneurysm treatment device is adapted to be placed attached to an artery of one of the following regions, the abdomen or thorax or arm or legs to treat an aneurysm in respectively region.

In a preferred embodiment, the aneurysm treatment device, comprising a power supply and an electronic circuitry adapted to power the cooling surface.

In a preferred embodiment, said power supply is a rechargeable power supply.

In a preferred embodiment, the cooling surface comprising an electronic element further creating heat on a second surface.

In a preferred embodiment, the electronic element is a peltier element.

In a preferred embodiment, the aneurysm treatment device, comprising a water cooling system adapted to transport away heat from the second surface.

In a preferred embodiment, the aneurysm treatment device, comprising a wireless energy transmitter for wireless charging of the power supply from outside the patients body.

In accordance with a fourth aspect of the present invention, there is provided a method for controlling hypertension in a human or mammal vascular system, the method comprising the steps of: inserting a needle like tube into the abdomen of the patients body, using the tube like needle like to fill the abdomen with gas thereby expanding the abdominal cavity, placing at least two laparoscopic trocars in the patient's body, inserting a camera through one of the trocars into the abdomen, inserting a dissecting tool through any of the trocar and dissecting an area of at least one portion of a blood vessel of the patient, placing a hypertension treatment device comprising a cooling surface, attached in relation to the blood vessel, and cooling a wall portion of the blood vessel to cause contraction of the wall portion to create a constriction of the blood vessel, to further influence a blood pressure difference before and after the constriction of the blood vessel. The blood vessel is preferably a arterial blood vessel leading from the abdominal aorta to an organ of the patient, wherein the hypertension treatment device is treating a high blood pressure in this vascular system.

In accordance with a fifth aspect of the present invention, there is provided a method for controlling hypertension locally in a human or mammal patients vascular system, the method comprising the steps of: inserting a needle like a tube into the thorax of the patients body, using the tube like needle to fill the thorax with gas thereby expanding the thoracal cavity, placing at least two laparoscopic trocars in the patient's body, inserting a camera through one of the trocars into the thorax, inserting a dissecting tool through any of the trocar and dissecting an area of at least one portion of a blood vessel, placing a hypertension treatment device comprising a cooling surface attached in relation to the blood vessel and cooling a wall portion of the blood vessel to cause contraction of the wall portion to create a constriction of the blood vessel, to further influence a blood pressure difference before and after the constriction of the blood vessel.

In accordance with a sixth aspect of the present invention, there is provided a method for controlling hypertension locally in a human or mammal patients vascular system, the method comprising the steps of: cutting the patients skin, dissecting the area of a blood vessel, placing a hypertension treatment device comprising a cooling surface attached in relation to the blood vessel and cooling a wall portion of the blood vessel to cause contraction of the wall portion to create a constriction of the blood vessel, to create a blood pressure difference before and after the constriction of the blood vessel.

In accordance with a seventh aspect of the present invention, there is provided a method for controlling hypotension locally in a human or mammal patients vascular system, the method comprising the steps of:

inserting a needle like a tube into the abdomen of the patients body, using the tube like needle to fill the abdomen with gas thereby expanding the thoracal cavity, placing at least two laparoscopic trocars in the patient's body, inserting a camera through one of the trocars into the abdomen, inserting a dissecting tool through any of the trocar and dissecting an area of at least one portion of a blood vessel, placing a hypotension treatment device comprising a heating surface attached in relation to the blood vessel and heating a wall portion of the blood vessel to cause dilatation of the wall portion to create a dilatation of the blood vessel, to further influence a blood pressure difference before and after the dilatation of the blood vessel.

In accordance with a eight aspect of the present invention, there is provided a method for controlling hypotension locally in a human or mammal patients vascular system, the method comprising the steps of: inserting a needle like a tube into the thorax of the patients body, using the tube like needle to fill the thorax with gas thereby expanding the thoracal cavity, placing at least two laparoscopic trocars in the patient's body, inserting a camera through one of the trocars into the thorax, inserting a dissecting tool through any of the trocar and dissecting an area of at least one portion of a blood vessel, placing a hypotension treatment device comprising a heating surface attached in relation to the blood vessel and heating a wall portion of the blood vessel to cause dilatation of the wall portion to create a dilatation of the blood vessel, to further influence a blood pressure difference before and after the dilatation of the blood vessel. The blood vessel is preferably a arterial blood vessel leading from the abdominal aorta to the kidney of the patient, wherein the hypotension treatment device is treating a low blood pressure in this renal vascular system.

In accordance with a ninth aspect of the present invention, there is provided a method for controlling hypotension locally in a human or mammal patients vascular system, the method comprising the steps of: cutting the patients skin, dissecting the area of a blood vessel, placing a hypotension treatment device comprising a heating surface attached in relation to the blood vessel and heating a wall portion of the blood vessel to cause dilatation of the wall portion to create a dilatation of the blood vessel, to create a blood pressure difference before and after the dilatation of the blood vessel.

In accordance with a tenth aspect of the present invention, there is provided a method for controlling an aneurysm locally in a human or mammal patients vascular system, the method comprising the steps of:

inserting a needle like tube into the abdomen of the patients body, using the tube like needle like to fill the abdomen with gas thereby expanding the abdominal cavity, placing at least two laparoscopic trocars in the patient's body, inserting a camera through one of the trocars into the abdomen, inserting a dissecting tool through any of the trocar and dissecting an area of at least one portion of an aneurysmatic blood vessel of the patient, placing a aneurysm treatment device comprising a cooling surface, attached in relation to the aneurysm, and cooling a wall portion of the blood vessel to cause contraction of the wall portion to create a constriction of the blood vessel, to treat the aneurysm by the constriction of the blood vessel.

In accordance with a eleventh aspect of the present invention, there is provided a method for controlling an aneurysm locally in a human or mammal patients vascular system, the method comprising the steps of:

inserting a needle like tube into the thorax of the patients body, using the tube like needle like to fill the thorax with gas thereby expanding the thoraxinal cavity, placing at least two laparoscopic trocars in the patient's body, inserting a camera through one of the trocars into the thorax, inserting a dissecting tool through any of the trocar and dissecting an area of at least one portion of an aneurysmatic blood vessel of the patient, placing a aneurysm treatment device comprising a cooling surface, attached in relation to the aneurysm, and cooling a wall portion of the blood vessel to cause contraction of the wall portion to create a constriction of the blood vessel, to treat the aneurysm by the constriction of the blood vessel.

In accordance with a twelfth aspect of the present invention, there is provided a method for controlling an aneurysm locally in a human or mammal patients vascular system, the method comprising the steps of:

cutting the patients skin, dissecting the area of a blood vessel, placing a aneurysm treatment device comprising a cooling surface attached in relation to the blood vessel and cooling a wall portion of the blood vessel to cause contraction of the wall portion to create a constriction of the blood vessel, to treat the aneurysm by the contraction of the blood vessel.

Thermal Stimulation

According to the invention, the treatment device thermally stimulates the wall portion of the organ. Thus, the control device may control the treatment device to cool the wall portion, to cause contraction of the wall portion. Alternatively, the control device may control the stimulation device to heat the wall portion to cause expansion of the wall portion. Where the wall portion includes a blood vessel, the control device may control the stimulation device to cool the blood vessel to cause contraction thereof, or heat the blood vessel to cause expansion thereof. Where applicable, thermal stimulation may be practiced in any of the embodiments of the present invention, and the thermal stimulation may be controlled in response to various sensors, for example strain, motion or pressure sensors.

In one embodiment, the treatment device is used in combination with a constriction device, such as a mechanical or hydraulic device, for thermally stimulating the wall portion of the blood vessel. Thus, the control device may control the stimulation device to cool the wall portion, when the wall portion is constricted, to cause contraction of the wall portion. For example, the constriction device may constrict the wall portion to at least restrict the flow in the lumen, and the control device may control the stimulation device to cool the constricted wall portion to cause contraction thereof, such that the flow in the lumen is at least further restricted, or further restricted but not stopped, or stopped. Alternatively, the control device may control the stimulation device to heat the wall portion, when the wall portion is constricted and contracted, to cause expansion of the wall portion. Where the wall portion includes a blood vessel, the control device may control the stimulation device to cool the blood vessel to cause contraction thereof, or heat the blood vessel to cause expansion thereof. Where applicable, thermal stimulation may be practiced in any of the embodiments of the present invention, and the thermal stimulation may be controlled in response to various sensors, for example strain, motion or pressure sensors.

The thermal stimulation may be used in combination with electrical stimulation of the wall portion of a blood vessel.

Sensor Controlled Treatment Device

As mentioned above, the system may comprise at least one implantable sensor, wherein the control device controls the treatment device and potentially a constriction device in response to signals from the sensor. Generally, the sensor directly or indirectly senses at least one physical parameter of the patient, or at least one functional parameter of the system.

Many different kinds of sensor for sensing physical parameters may be used. For example motion sensors for sensing organ motion, i.e. natural contractions, such as stomach or intestinal contractions, pressure sensors for sensing pressure in the organ, strain sensors for sensing strain of the organ, flow sensors for sensing fluid flow in the lumen of the organ, spectro-photometrical sensors, Ph-sensors for sensing acidity or alkalinity of the fluid in the lumen of the organ, oxygen-sensors sensors for sensing the oxygen content of the fluid in the lumen of the organ, or sensors for sensing the distribution of the stimulation on the stimulated organ. Any conceivable sensors for sensing any other kind of useful physical parameter may be used.

Many different kinds of sensors that sense functional parameters of the apparatus may also be used for the control of the constriction device and/or the thermal stimulation device. For example sensors for sensing electric parameters of implanted electric components of the apparatus, or sensors for sensing the performance of implanted motors of the apparatus.

The sensor may comprise a pressure sensor for sensing as the physical parameter a pressure in the patient's body that relates to the pressure in the lumen of the patient's bodily organ, wherein the control device controls the constriction device and/or stimulation device to change the constriction of the patient's blood vessel wall portion in response to the pressure sensor sensing a predetermined value of measured pressure.

Alternatively, or in combination with the pressure sensor, a position sensor may be provided for sensing as the physical parameter the orientation of the patient with respect to the horizontal. The position sensor may be a biocompatible version of what is shown in U.S. Pat. Nos. 4,942,668 and 5,900,909. For example, the control device may control the constriction device and/or stimulation device to change the constriction of the patient's wall portion in response to the position sensor sensing that the patient has assumed a substantially horizontal orientation, i.e. that the patient is lying down.

The above described sensors may be used in any of the embodiments of the invention, where applicable.

The control device may control the constriction device and/or stimulation device to change the constriction of the patient's wall portion in response to the time of day. For that purpose the control device may include a clock mechanism for controlling the constriction device and/or stimulation device to change the constriction of the patient's wall portion to increase or decrease the influence on the flow in the lumen during different time periods of the day. In case a sensor of any of the above-described types for sensing a physical or functional parameter is provided, either the clock mechanism is used for controlling the constriction device and/or stimulation device provided that the parameter sensed by the sensor does not override the clock mechanism, or the sensor is used for controlling the constriction device and/or stimulation device provided that the clock mechanism does not override the sensor. Suitably, the control device produces an indication, such as a sound signal or displayed information, in response to signals from the sensor.

The control device may comprise an implantable internal control unit that directly controls the constriction device and/or thermal stimulation device in response to signals from the sensor. The control device may further comprise a wireless remote control adapted to set control parameters of the internal control unit from outside the patient without mechanically penetrating the patient. At least one of the control parameters, which is sellable by the wireless remote control, is the physical or functional parameter. Suitably, the internal control unit includes the above mentioned clock mechanism, wherein the wireless remote control also is adapted to set the clock mechanism.

Alternatively, the control device may comprise an external control unit outside the patient's body for controlling the constriction device and/or stimulation device in response to signals from the sensor.

Mechanical Operation

Where the system comprises a constriction device, an operation device may mechanically operate the constriction device, which may be non-inflatable. Furthermore, the operation device may comprise a servo system, which may include a gearbox. The term "servo system" encompasses the normal definition of a servo mechanism, i.e., an automatic device that controls large amounts of power by means of very small amounts of power, but may alternatively or additionally encompass the definition of a mechanism that transfers a weak force acting on a moving element having a long stroke into a strong force acting on another moving element having a short stroke. Preferably, the operation device operates the constriction device in a non-magnetic and/or non-manual manner. A motor may be operatively connected to the operation device. The operation device may be operable to perform at least one reversible function and the motor may be capable of reversing the function.

Hydraulic Operation

Where the system comprises a constriction device, an operation device may hydraulically operate the constriction device In an embodiment of the invention, the hydraulic means comprises a reservoir and an expandable/contractible cavity in the constriction device, wherein the operation device distributes hydraulic fluid from the reservoir to expand the cavity, and distributes hydraulic fluid from the cavity to the reservoir to contract the cavity. The cavity may be defined by a balloon of the constriction device that abuts the tissue wall portion of the patient's organ, so that the patient's wall portion is constricted upon expansion of the cavity and released upon contraction of the cavity.

Alternatively, the cavity may be defined by a bellows that displaces a relatively large contraction element of the constriction device, for example a large balloon that abuts the wall portion, so that the patient's wall portion is constricted upon contraction of the bellows and released upon expansion of the bellows. Thus, a relatively small addition of hydraulic fluid to the bellows causes a relatively large increase in the constriction of the wall portion. Such a bellows may also be replaced by a suitably designed piston/cylinder mechanism.

Design of Control Device

The control device suitably controls the treatment device from outside the patient's body. Preferably, the control device is operable by the patient. For example, the control device may comprise a manually operable switch for switching on and off the treatment device, wherein the switch is adapted for subcutaneous implantation in the patient to be manually or magnetically operated from outside the patient's body. Alternatively, the control device may comprise a hand-held wireless remote control, which is conveniently operable by the patient to switch on and off the treatment device. The wireless remote control may also be designed for application on the patient's body like a wristwatch. Such a wristwatch type of remote control may emit a control signal that follows the patient's body to implanted signal responsive means of the apparatus.

Where the control device wirelessly controls the treatment device from outside the patient's body, the wireless control function is preferably performed in a non-magnetic manner, i.e., the control device controls the constriction device of the treatment device in a non-magnetic manner. The patient may use the remote control to control the treatment device to adjust the stimulation intensity and/or adjust the constriction of the wall portion. The wireless remote control may comprise at least one external signal transmitter or transceiver and at least one internal signal receiver or transceiver implantable in the patient.

The wireless remote control preferably transmits at least one wireless control signal for controlling the treatment device. The control signal may comprise a frequency, amplitude, phase modulated signal or a combination thereof, and may be an analogue or a digital signal, or a combination of an analogue and digital signal. The remote control may transmit an electromagnetic carrier wave signal for carrying the digital or analogue control signal. Also the carrier signal may comprise digital, analogue or a combination of digital and analogue signals.

Any of the above control signals may comprise wave signals, for example a sound wave signal, an ultrasound wave signal, an electromagnetic wave signal, an infrared light signal, a visible light signal, an ultra violet light signal, a laser light signal, a microwave signal, a radio wave signal, an x-ray radiation signal or a gamma radiation signal. Alternatively, the control signal may comprise an electric or magnetic field, or a combined electric and magnetic field.

As mentioned above, the control signal may follow the patient's body to implanted signal responsive means of the apparatus.

The control device may include a programmable internal control unit, such as a microprocessor, implantable in the patient for controlling the treatment device. The control device may further include an external control unit intended to be outside the patient's body, wherein the internal control unit is programmable by the external control unit. For example, the internal control unit may be programmable for controlling the treatment device over time, suitably in accordance with an activity schedule program. The apparatus of the invention may comprise an external data communicator and an implantable internal data communicator communicating with the external data communicator, wherein the internal communicator feeds data related to the treatment device back to the external data communicator or the external data communicator feeds data to the internal data communicator.

Source of Energy

The present invention also presents a solution for supplying energy for use in connection with the operation of the treatment device. Thus, in a broad sense, the present invention provides an apparatus for controlling a flow of blood in a blood vessel a patient's organ, wherein the system may comprise an implantable constriction device for gently constricting a portion of the tissue wall to influence the flow in the blood vessela source of energy, and a control device operable from outside the patient's body to control the source of energy to release energy for use in connection with the operation of the system. In a simple form of the invention, the source of energy, such as a battery or accumulator, is implantable in the patient's body.

Transmission of Wireless Enemy

In a more sophisticated form of the invention, which is preferable, the source of energy is external to the patient's body and the control device controls the external source of energy to release wireless energy. In this sophisticated form of the invention, the apparatus comprises an energy-transmission device that transmits the released wireless energy from outside the patient's body to inside the patient's body. Among many things the wireless energy may comprise electromagnetic energy, an electric field, an electromagnetic field or a magnetic field, or a combination thereof, or electromagnetic waves. The energy-transmission device may transmit wireless energy for direct use in connection with the operation of the treatment device, as the wireless energy is being transmitted. For example, where an electric motor or pump operates the constriction device, wireless energy in the form of a magnetic or an electromagnetic field may be used for direct power of the motor or pump.

Thus, the motor or pump is running directly during transmission of the wireless energy. This may be achieved in two different ways: a) using a transforming device implanted in the patient to transform the wireless energy into energy of a different form, preferably electric energy, and powering the motor or pump with the transformed energy, or b) using the wirelessly transmitted energy to directly power the motor or pump. Preferably wireless energy in the form of an electromagnetic or magnetic field is used to directly influence specific components of the motor or pump to create kinetic energy for driving the motor or pump. Such components may include coils integrated in the motor or pump, or materials influenced by magnetic fields, or permanent magnets, wherein the magnetic or electromagnetic field influences the coils to generate a current for driving the motor or pump, or influences the material or permanent magnets to create kinetic energy for driving the motor or pump.

Preferably, the energy-transmission device transmits energy by at least one wireless signal, suitably a wave signal. The wave signal may comprise an electromagnetic wave signal including one of an infrared light signal, a visible light signal, an ultra violet light signal, a laser signal, a microwave signal, a radio wave signal, an x-ray radiation signal, and a gamma radiation signal. Alternatively, the wave signal may comprise a sound or ultrasound wave signal. The wireless signal may be a digital or analogue signal, or a combination of a digital and analogue signal.

Transforming Wireless Energy

In accordance with a particular embodiment of the invention, an implantable energy-transforming device is provided for transforming wireless energy of a first form transmitted by the energy-transmission device into energy of a second form, which typically is different from the energy of the first form. The treatment device is operable in response to the energy of the second form. For example, the wireless energy of the first form may comprise sound waves, whereas the energy of the second form may comprise electric energy. In this case, the energy-transforming device may include a piezo-electric element for transforming the sound waves into electric energy. Optionally, one of the energy of the first form and the energy of the second form may comprise magnetic energy, kinetic energy, sound energy, chemical energy, radiant energy, electromagnetic energy, photo energy, nuclear energy or thermal energy. Preferably, one of the energy of the first form and the energy of the second form is non-magnetic, non-kinetic, non-chemical, non-sonic, non-nuclear or non-thermal.

The energy-transforming device may function differently from or similar to the energy-transmission device. In a special embodiment, the energy-transforming device comprises at least one element, such as at least one semiconductor, having a positive region and a negative region, when exposed to the energy of the first form transmitted by the energy-transmission device, wherein the element is capable of creating an energy field between the positive and negative regions, and the energy field produces the energy of the second form. More specifically, the element may comprise an electrical junction element, which is capable of inducing an electric field between the positive and negative regions when exposed to the energy of the first form transmitted by the energy-transmission device, whereby the energy of the second form comprises electric energy.

The energy-transforming device may transform the energy of the first form directly or indirectly into the energy of the second form. An implantable motor or pump for operating the constriction device of the treatment device may be provided, wherein the motor or pump is powered by the energy of the second form. The constriction device may be operable to perform at least one reversible function and the motor may be capable of reversing the function. For example, the control device may shift polarity of the energy of the second form to reverse the motor.

The energy-transforming device may directly power the motor or pump with the transformed energy, as the energy of the second form is being transformed from the energy of the first form. Preferably, the energy-transforming device directly operates the treatment device with the energy of the second form in a non-magnetic, non-thermal or non-mechanical manner.

Normally, the treatment device comprises electric components that are energized with electrical energy. Other implantable electric components of the apparatus may be at least one voltage level guard or at least one constant current guard. Therefore, the energy-transforming device may transform the energy of the first form into a direct current or pulsating direct current, or a combination of a direct current and pulsating direct current. Alternatively, the energy-transforming device may transform the energy of the first form into an alternating current or a combination of a direct and alternating current.

The apparatus of the invention may comprise an internal source of energy implantable in the patient for supplying energy for the operation of the treatment device. The apparatus may further comprise an implantable switch operable to switch from an "off" mode, in which the internal source of energy is not in use, to an "on" mode, in which the internal source of energy supplies energy for the operation of the treatment device, and/or for energizing implanted electronic components of the apparatus. The switch may be operable by the energy of the first form transmitted by the energy-transmission device or by the energy of the second form supplied by the energy-transforming device. The described switch arrangement reduces power consumption of the apparatus between operations.

The internal source of energy may store the energy of the second form supplied by the energy-transforming device. In this case, the internal source of energy suitably comprises an accumulator, such as at least one capacitor or at least one rechargeable battery, or a combination of at least one capacitor and at least one rechargeable battery. Where the internal source of energy is a rechargeable battery it may be charged only at times convenient for the patient, for example when the patient is sleeping. Alternatively, the internal source of energy may supply energy for the operation of the treatment device but not be used for storing the energy of the second form. In this alternative, the internal source of energy may be a battery and the switch described above may or may not be provided.

Suitably, the system of the invention comprises an implantable stabilizer for stabilizing the energy of the second form. Where the energy of the second form is electric energy the stabilizer suitably comprises at least one capacitor.

The energy-transforming device may be designed for implantation subcutaneously in the abdomen, thorax or cephalic region of the patient. Alternatively, it may be designed for implantation in an orifice of the patient's body and under the mucosa or intramuscularly outside the mucosa of the orifice.

Although the treatment device in the embodiments described above is designed as a single piece, which is most practical for implantation, it should be noted that as an alternative the constriction device and stimulation device could be designed as separate pieces. Any one of the constriction and stimulation units described above may alternatively be replaced by two or more separate constriction/stimulation elements, which are controlled independently of one another.

The present invention also provides a method for using a system as described above to control the blood flow in the blood vessel of a patient's organ.

DETAILED DESCRIPTION OF THE INVENTION

Referring to the drawing figures, like reference numerals designate identical or corresponding elements throughout the several figures.

Figure 1A:
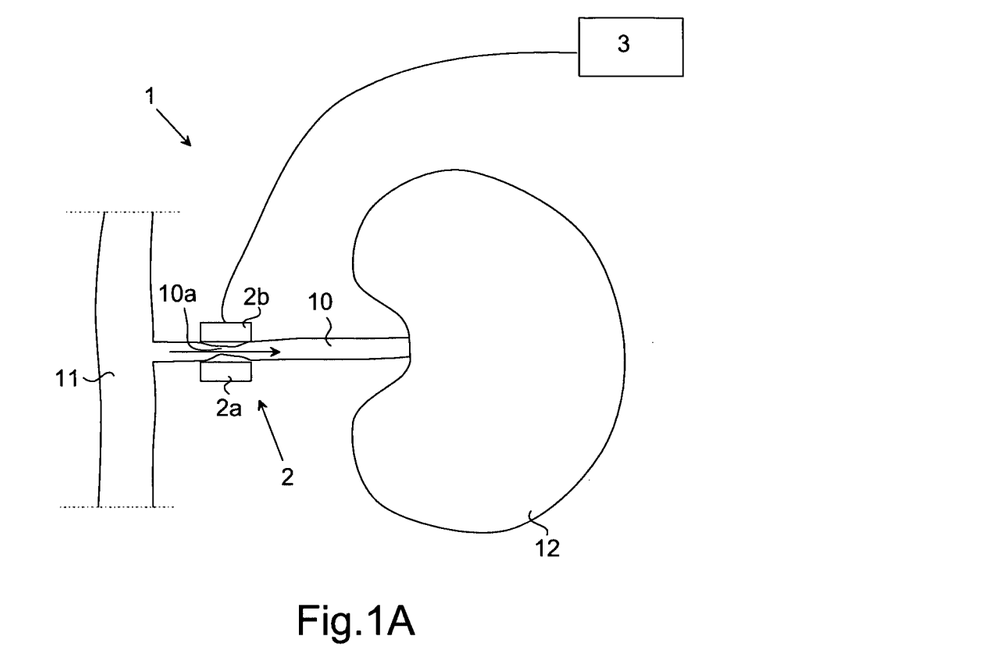
FIG. 1A schematically shows a first embodiment of a system according to the invention in a non-operative mode.

FIG. 1 illustrates an embodiment of a system according to the invention, generally designated 1. The system comprises thermal elements 2a, 2b of a hypotension treatment device 2 are provided so as to thermally heat an arterial blood vessel 10, i.e., a renal artery leading from the abdominal aorta 11 to the kidney 12 of a patient, wherein the hypotension treatment device is treating a low blood pressure in this renal vascular system. A control device 3 is connected to the hypotension treatment device 2 such as to control the operation thereof, i.e., the temperature of the thermal elements 2a, 2b.

In the figure, a constriction 10a of the renal artery 10 is shown. This constriction creates a lower blood pressure downstream of the constriction than upstream thereof, as indicated by the arrow. This means in turn that the kidney 12 will perceive a low blood pressure, affecting the operation thereof negatively.

Figure 1B:
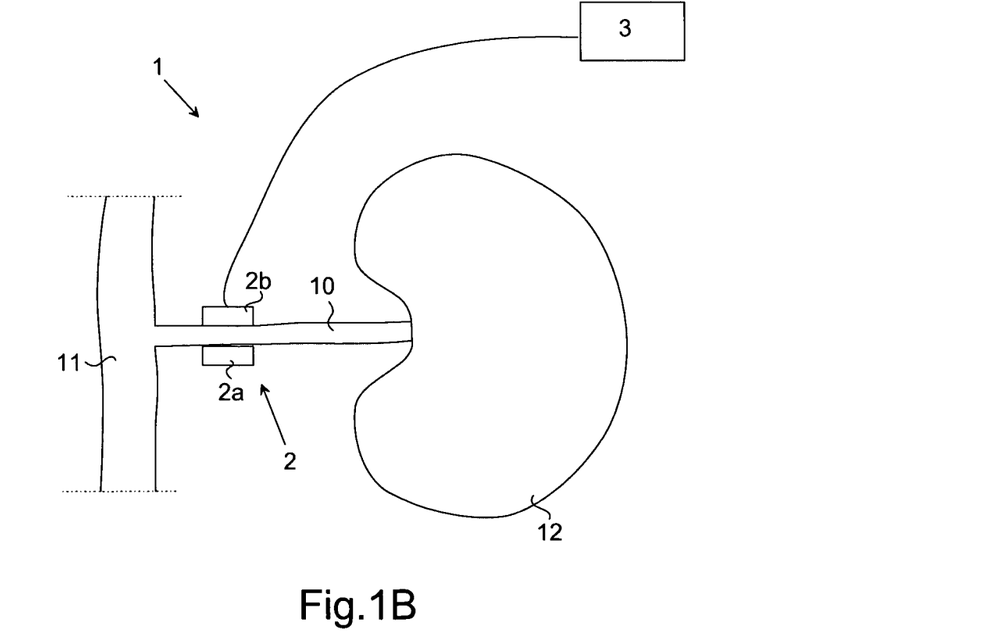
FIG. 1B show the embodiment of FIG. 1A in an operative mode.

In order to remedy this situation, the hypotension treatment device 2 is operated by the control device 3 so that the thermal elements 2a, 2b are heated, in turn heating the renal artery 10 locally at the constriction 10a thereof. This operational mode is shown in FIG. 1B, where it can be seen that a dilatation of the blood vessel 10 is achieved at the point of the constriction 10a, allowing the blood to flow freely within the renal artery and thereby increasing the blood pressure in the kidney 12.

Figure 2A:
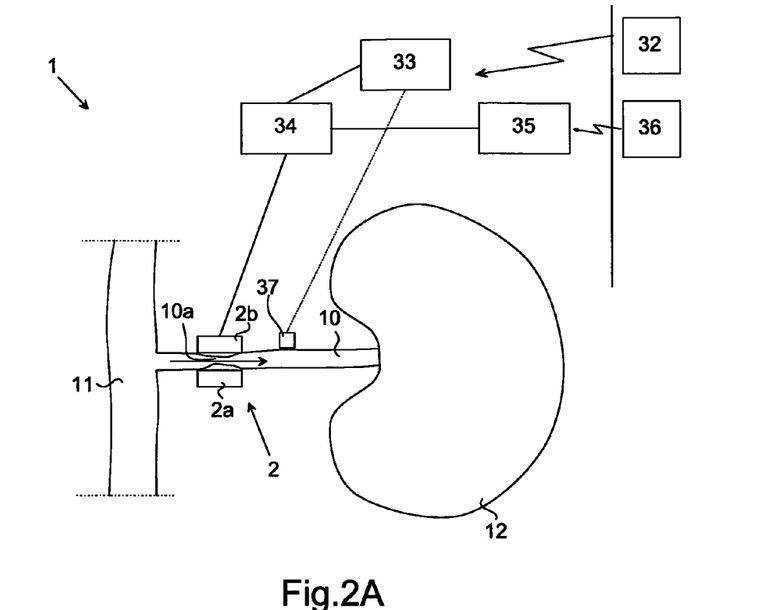
FIG. 2A schematically shows a second embodiment of a system according to the invention in a non-operative mode.
Figure 2B:
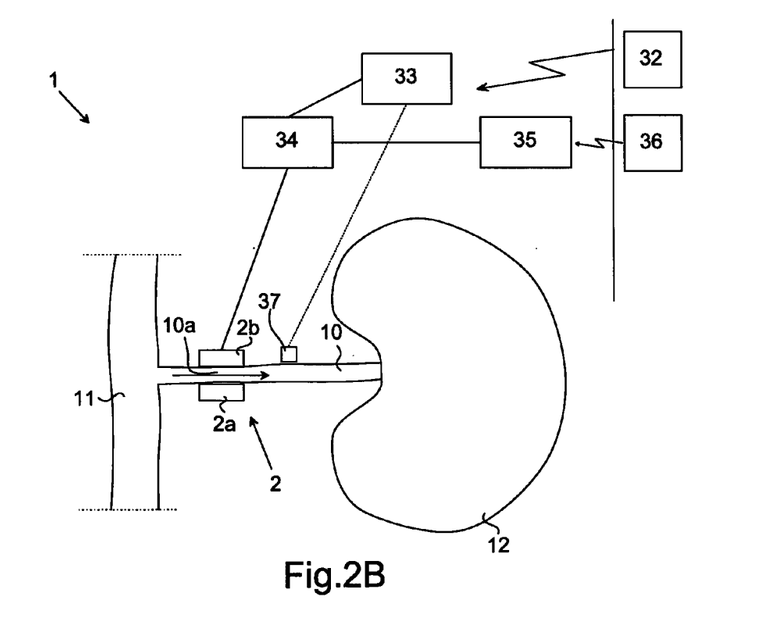
FIG. 2B show the embodiment of FIG. 2A in an operative mode.

An alternative embodiment of a system according to the invention will now be described with reference to FIGS. 2A and 2B. In many aspects this embodiment is identical to the one described above with reference to FIGS. 1A and 1B. However, in this second embodiment, the control device includes an external control unit in the form of a hand-held wireless remote control 32, and an implanted internal control unit 33, which may include a microprocessor, for controlling the constriction and stimulation devices. The remote control 32 is operable by the patient to control the internal control unit 33 to switch on and off the treatment device. Alternatively, however, the remote control 32 may be replaced by a subcutaneously implanted push button that is manually switched by the patient between "on" and "off". Such a manually operable push button may also be provided in combination with the remote control 32 as an emergency button to allow the patient to stop the operation of the apparatus in case of emergency or malfunction.

The internal control unit 33 controls an implanted operation device 34 to operate the treatment device 2. An implanted source of energy 35, such as a rechargeable battery, powers the operation device 34. The internal control unit 33, which may be implanted subcutaneously or in the abdomen, may also work as an energy receiver, i.e., for transforming wireless energy into electric energy and charging the implanted source of energy 35 (rechargeable battery) with the electric energy. Alternatively, a separate external charging unit 36 is provided to wirelessly charge the source of energy 35.

An implanted sensor 37 senses the blood pressure of the patient downstream of the constriction 10a and the internal control unit 33 controls the treatment device 2 in response to signals from the sensor 37. In this embodiment the sensor 37 is a pressure sensor The remote control 32 may be equipped with means for producing an indication, such as a sound signal or displayed information, in response to signals from the sensor 37. When the patient's attention is taken by such an indication indicating an increased pressure exceeding a threshold value, he or she may use the remote control to control the constriction device and stimulation device to pump intestinal contents through the patient's stoma.

Figure 3A:
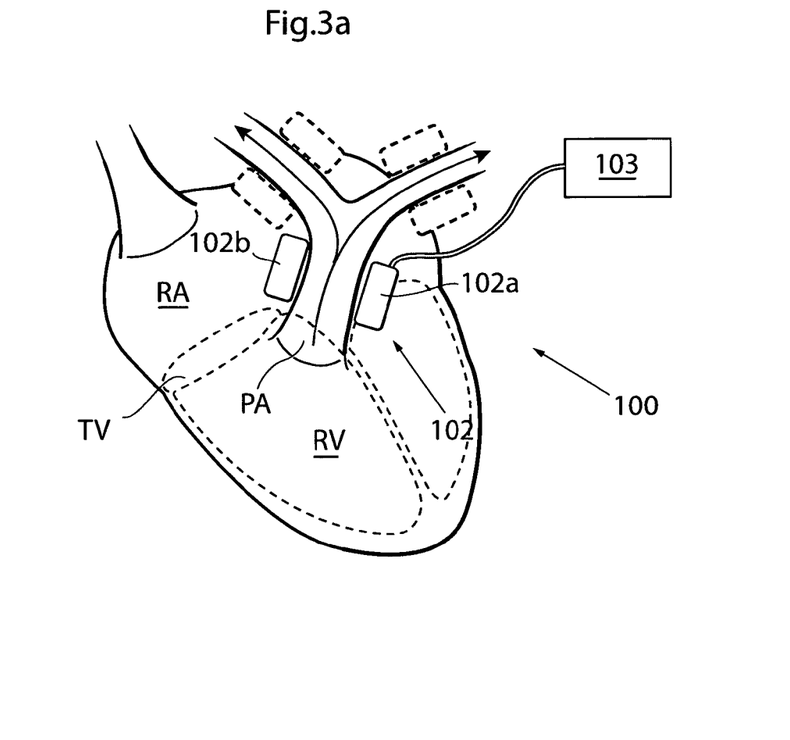
FIG. 3A schematically shows a third embodiment of a system according to the invention in a non-operative mode.
Figure 3B:
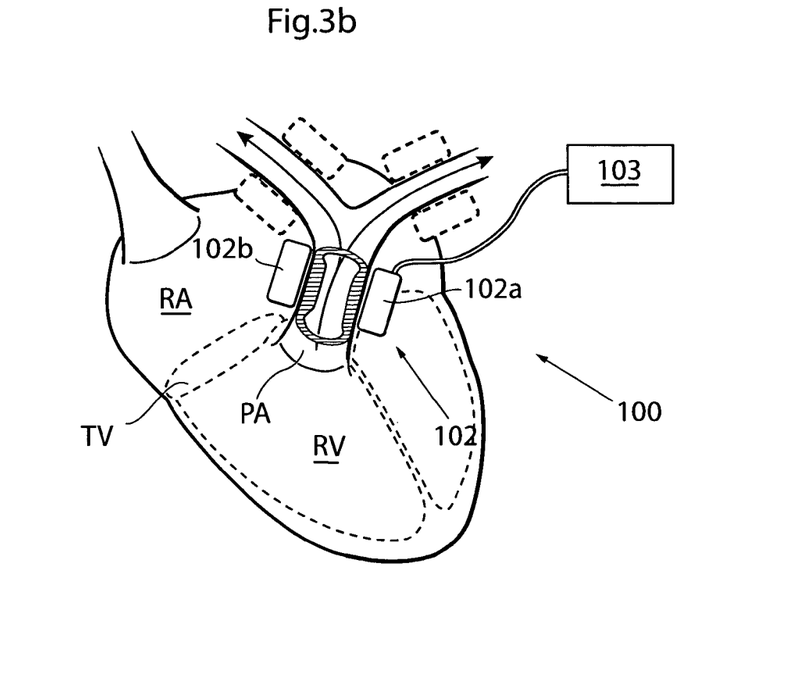
FIG. 3B show the embodiment of FIG. 3A in an operative mode.

The embodiment shown in FIGS. 3A and 3B is a system for treating high blood pressure. Turning first to FIG. 3A, a human heart of a patient is shown and the operation of the right heart pump will now be described, the left heart pump being outlined with dashed lines. The right heart pump consists of the right atrium (RA), tricuspid valve (TV), right ventricle (RV), pulmonic valve (PV), and pulmonary artery (PA). Poorly oxygenated blood returning to the heart from the body's organs enters the right atrium, and is stored there until the right atrium contracts. When the right atrium contracts, the tricuspid valve opens, allowing the blood to enter the right ventricle. Then, when the right ventricle contracts, the pulmonic valve opens, and the blood is propelled into the pulmonary artery. The pulmonary artery carries the blood to the lungs, where it picks up oxygen.

When a treatment device of a system according to the invention is applied to a blood vessel leading from the right heart chamber to the lung of the patient, i.e., the pulmonary artery, the treatment device functions as a hypertension treatment device for treating a high blood pressure in this pulmonary vascular system. The system, generally designated 100, then comprises a treatment device 102 comprising thermal elements 102a, 102b operating under control of a control device 103.

Turning now to FIG. 3B, in order to lower the pressure of the blood leaving the pulmonary artery, the thermal elements 102a, 102b, are cooled, thereby cooling the walls of the pulmonary artery. This in turn result in a constriction of the pulmonary artery locally at the treatment device, which lower the pressure of the blood downstream of the treatment device.

Alternative positions of the treatment device after the bifurcation of the pulmonary artery are shown with dashed lines in the FIGS. 3A and 3B.

It will be realized that the application described above with reference to FIGS. 3A and 3B can also be implemented with the devices described above with reference to FIGS. 2A and 2B.

Figures 4A, 4B:
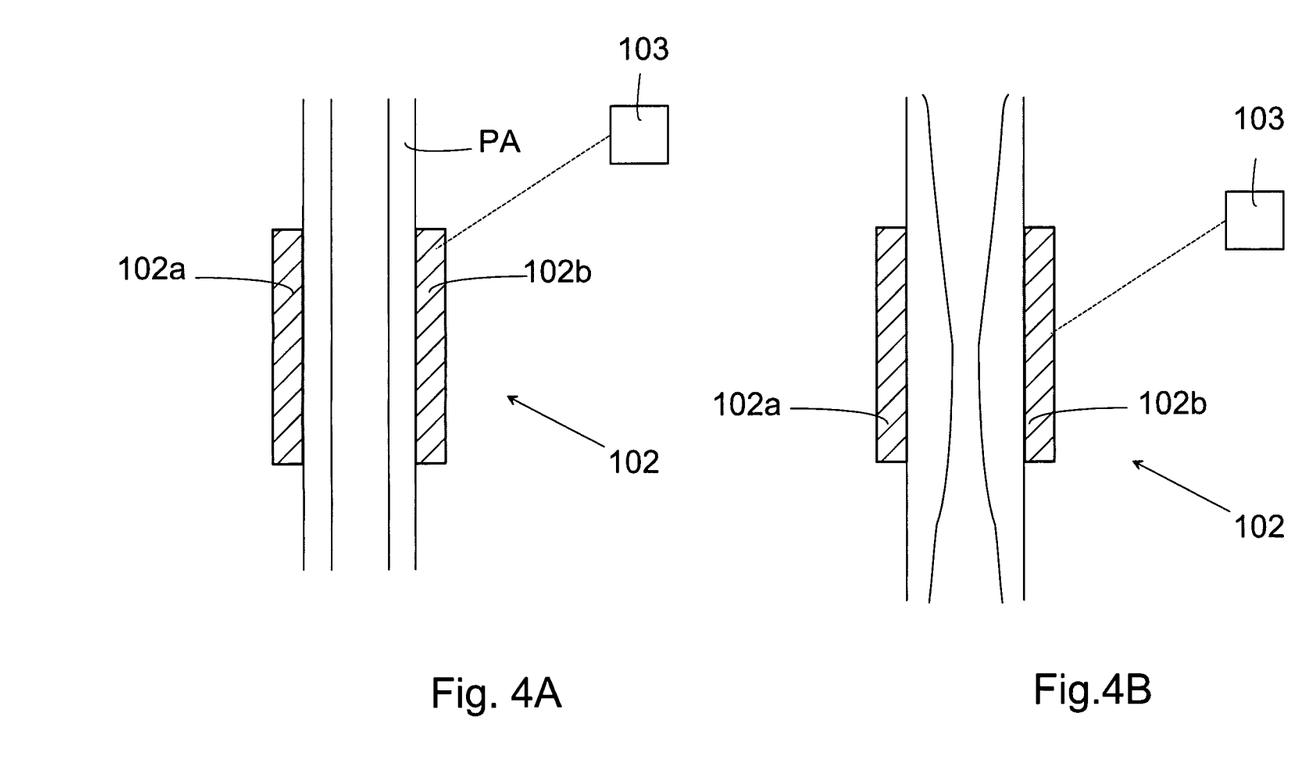
FIG. 4A is a detailed view of a treatment device of a system according to the invention in a non-operative mode.
FIG. 4B is a view similar to that of FIG. 4A but with the treatment device in an operative mode.

FIGS. 4A and 4B show an embodiment of the treatment device that controls blood flow in a blood vessel, such as the pulmonary artery PA. The treatment device comprises a stimulation device in the form of two thermal stimulation elements 102a and 102b. A control device 3 for controlling the thermal stimulation elements 102a, 102b is also shown in the figures. to constrict and releaser, respectively, the blood vessel. The thermal stimulation elements 102a and 102b, which may include Peltier elements, are positioned so that the thermal element 102a is facing the thermal element 102b. FIG. 4A shows the treatment device in a non-operating state, wherein the blood flow is unaffected. FIG. 4B shows how the control device 3 controls the thermal stimulation elements 102a, 102b to cool the wall of the blood vessel PA, so that the wall contracts and partly closes the blood vessel PA. To release the blood vessel PA, the control device 3 controls the thermal stimulation elements 102a, 102b to heat the wall of the blood vessel PA, so that the wall expands.

The treatment device shown in FIGS. 4A and 4B lends itself also for treatment of aneurysm, i.e., a localized, blood-filled dilation (bulge) of a blood vessel caused by disease or weakening of the vessel wall.

Figure 5A:
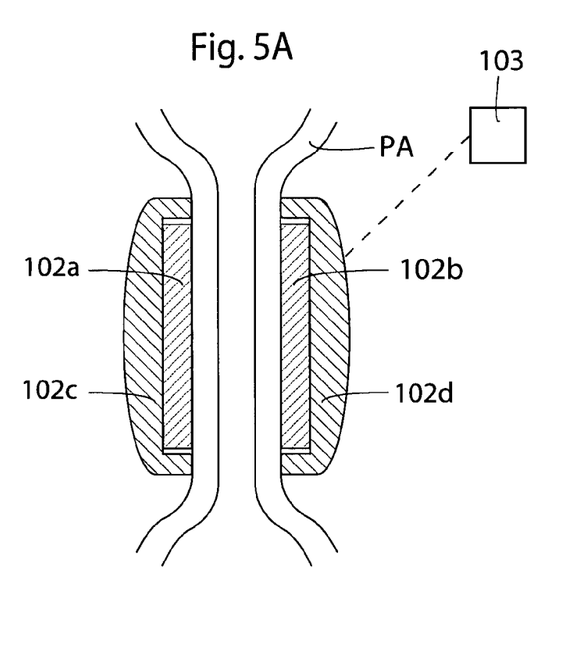
FIG. 5A is a detailed view of an alternative treatment device of a system according to the invention in a non-operative mode.
Figure 5B:
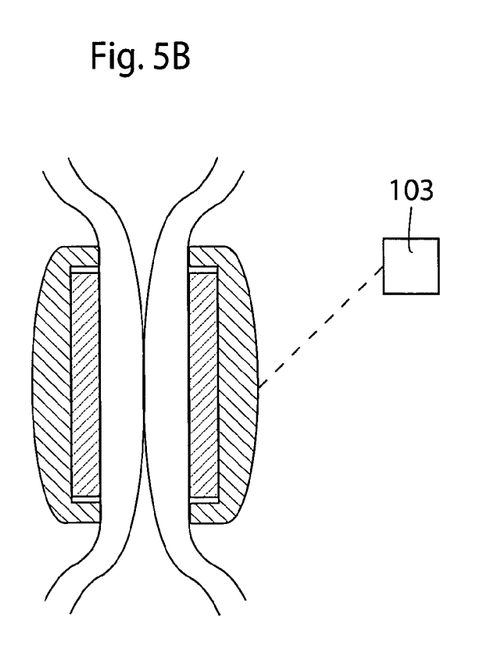
FIG. 5B is a view similar to that of FIG. 5A but with the alternative treatment device in an operative mode.

FIGS. 5A and 5B show another embodiment of the treatment device that controls blood flow in a blood vessel, such as the pulmonary artery PA. The treatment device comprises a constriction device with two clamping elements 102c and 102d, a stimulation device in the form of two thermal stimulation elements 102a and 102b. A control device 3 for controlling the thermal stimulation elements 102a, 102b and the clamping elements 102c, 102d is also shown in the figures. The clamping elements 102c and 102d are movable towards and away from each other to constrict and release, respectively, the blood vessel. The thermal stimulation elements 102a and 102b, which may include Peltier elements, are positioned so that the thermal element 102a is facing the thermal element 102b. FIG. 4A shows how the clamping elements 102c, 102d constrict the blood vessel PA, so that the blood flow is restricted. FIG. 5B shows how the control device 103 controls the thermal stimulation elements 102a, 102b to cool the wall of the blood vessel PA, so that the wall contracts and further closes the blood vessel PA. To release the blood vessel PA, the control device 103 controls the thermal stimulation elements 102a, 102b to heat the wall of the blood vessel PA, so that the wall expands and the clamping elements may be moved from each other.

Figure 6A:
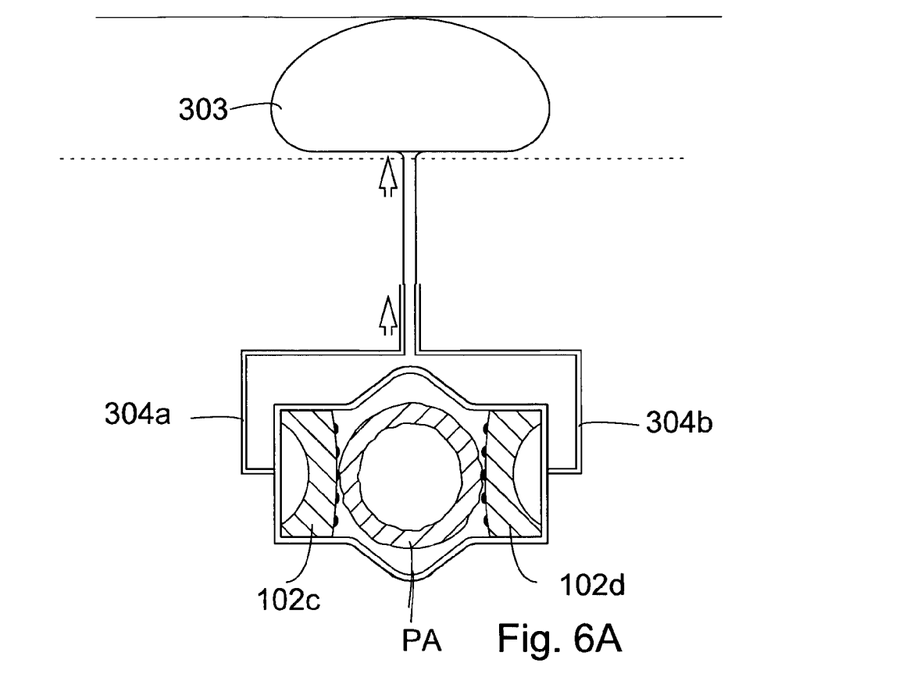
FIG. 6A is a schematic view of hydraulic operation means suited for operating the treatment device of the embodiments of FIGS. 4A, 4B, 5A, and 5B.
Figure 6B:
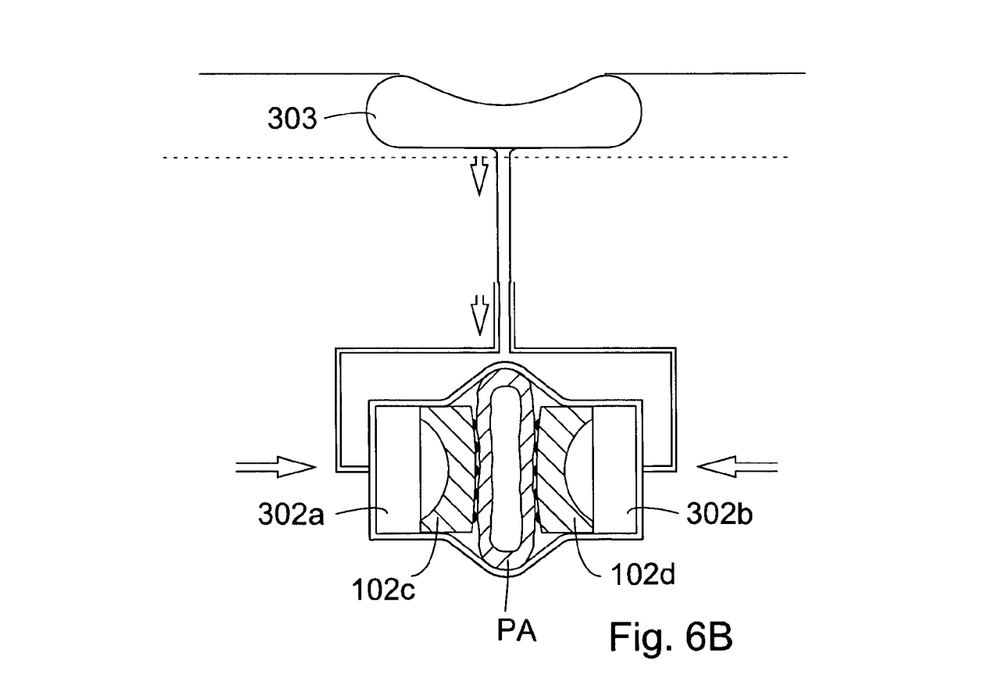
FIG. 6B shows the embodiment of FIG. 6A with the treatment device constricting a blood vessel of a patient.

FIGS. 6A and 6B show hydraulic operation means suited for operating the constriction device of the embodiments described above. Specifically, FIGS. 6A and 6B show the apparatus of FIGS. 5A, 5B provided with such means for hydraulic operation of the constriction device in the form of clamping elements 102c, 102d. Thus, the housing 300 forms two hydraulic chambers 302a and 302b, in which the two clamping elements 102c, 102d are slidable back and forth relative to the tubular wall portion 8 of a patient's blood vessel. The hydraulic operation means include an expandable reservoir 303, such as an elastic balloon, containing hydraulic fluid, and conduits 304a and 304b between the reservoir 303 and the hydraulic chambers 302a, 302b By pressing the reservoir 303, the tubular wall portion PA is constricted, see FIG. 6B, and to pump hydraulic fluid from the chambers 302a, 302b to the reservoir 303 to move the clamping elements away from the wall portion, whereby the blood vessel is released, see FIG. 6A.

Figure 7A:
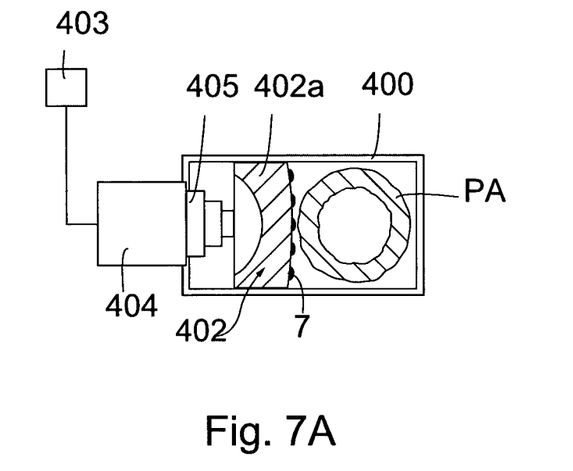
FIG. 7A is a schematic view of mechanical operation means suited for operating the treatment device of the embodiments of FIGS. 4A, 4B, 5A, and 5B.
Figure 7B:
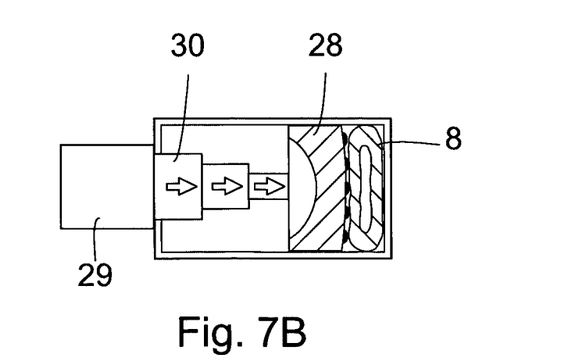
FIG. 7B shows the embodiment of FIG. 7A with the constriction device constricting a blood vessel of a patient.

FIGS. 7A and 7B schematically show a mechanically operable embodiment of the invention, comprising an open ended tubular housing 400 applied on the tubular tissue wall portion of a patient's blood vessel, a constriction device 402 arranged in the housing 400 and a control device 403 for controlling the constriction device 402. A thermal stimulation device (not shown) as described above is also provided in the housing 400. The constriction device 402 includes a clamping element 402a, which is radially movable in the tubular housing 400 towards and away from the tubular wall portion PA between a retracted position, see FIG. 7A, and a clamping position, see FIG. 7B, in which the clamping element 402a gently constricts the tubular wall portion PA. Mechanical operation means for mechanically operating the clamping element 402a includes an electric motor 404 attached to the housing 400 and a telescopic device 405, which is driven by the motor 404 and operatively connected to the clamping element 402a. The control device 403 controls the electric motor 404 to expand the telescopic device 405 to move the clamping element 402a against the wall portion PA, whereby the tubular wall portion is constricted, see FIG. 7B, and controls the motor 404 to retract the telescopic device 405 to move the clamping element 402a away from the wall portion, whereby the wall portion is released, see FIG. 7A.

Figure 7C:
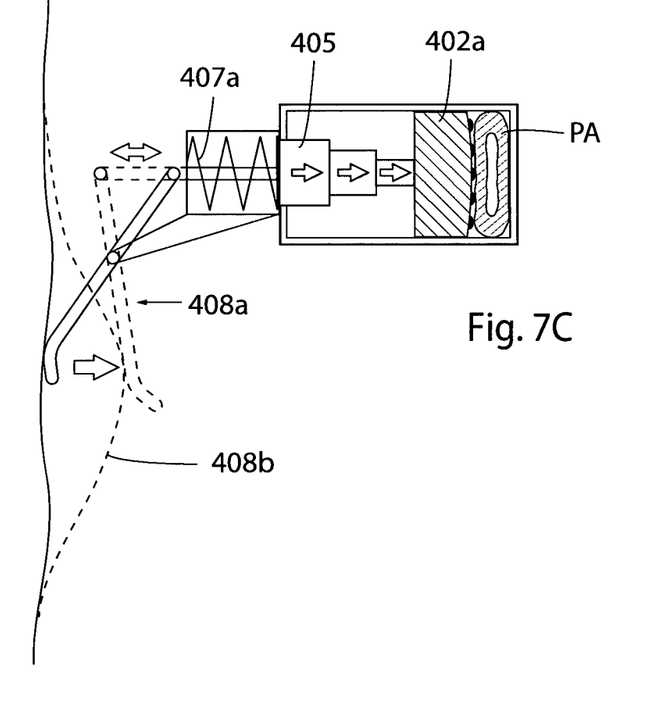
FIG. 7C shows a modification of the embodiment of FIG. 7B.

Alternatively, the motor may be omitted and the telescopic device 405 be modified for manual operation, as shown in FIG. 7C. Thus, a spring 407a may be provided acting to keep the telescopic device 405 expanded to force the clamping element 402a against the wall portion PA. The mechanical operation means may include a subcutaneously implanted lever mechanism 408a that is operatively connected to the telescopic device 405. The patient may push the lever mechanism 408a through the patient's skin 408b to pull the telescopic device 405 against the action of the spring 407a to the retracted position of the telescopic device 405, as indicated in phantom lines. When the patient releases the lever mechanism 408a, the spring 407a expands the telescopic device 405, whereby clamping element 402 is forced against the wall portion PA.

Figure 8A:
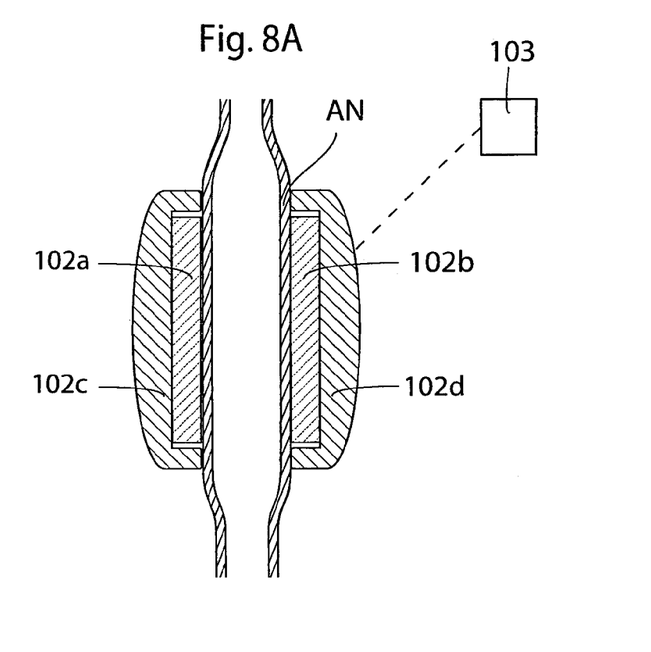
FIGS. 8A and 8B show an embodiment of the treatment device that aneurysm in a blood vessel, such as for example the aorta.
Figure 8B:
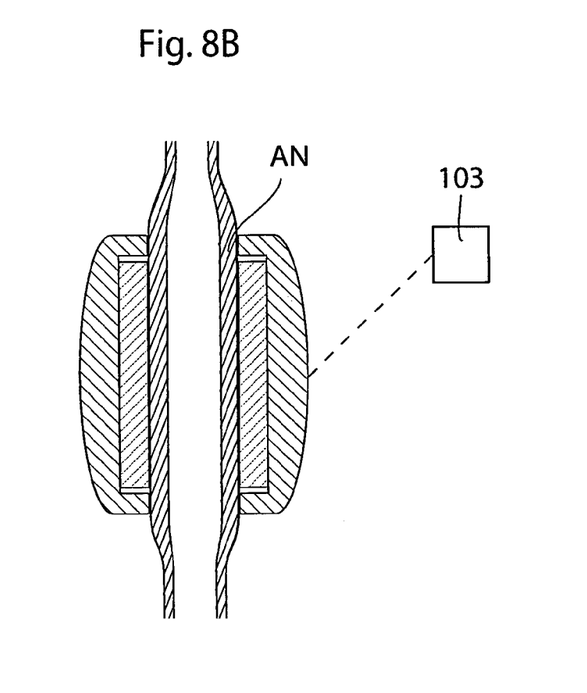

FIGS. 8A and 8B show an embodiment of the treatment device that aneurysm in a blood vessel, such as the aorta. The treatment device comprises a stimulation device in the form of two thermal stimulation elements 102a and 102b. A control device 103 for controlling the thermal stimulation elements 102a, 102b is also shown in the figures. to constrict and releaser, respectively, the blood vessel. The thermal stimulation elements 102a and 102b, which may include Peltier elements, are positioned so that the thermal element 102a is facing the thermal element 102b. FIGURE (A shows the treatment device in a non-operating state, wherein the blood flow is unaffected. FIGURE (B shows how the control device 103 controls the thermal stimulation elements 102a, 102b to cool the wall of the blood vessel aneurysm AN, so that the wall contracts and partly reduces the dilatation of the aneurysmatic blood vessel. In reality it may be enough that the tonus of the aneurysmatic wall increases to minimize the risk of such aneurysm to expand. The drawing may therefore be seen as very exaggerated to understand the principle. To release the blood vessel, the control device 103 controls the thermal stimulation elements 102a, 102b to stop cooling the wall of the blood vessel, so that the wall expands.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A system for treating a patient with general hypertension by increasing a blood flow in the renal artery, the system comprising:
   a hypertension treatment device adapted to:
      have at least one surface of the device placed on the outside of the renal artery to increase the blood flow in the patient's renal region, wherein said surface comprises a heating surface able to heat said renal artery to dilate said renal artery and thereby increase the blood flow distal to said dilated renal artery, causing the kidney to reduce the general blood pressure and thereby treat general hypertension, and to
      be used in combination with a constriction device, when thermally stimulating the wall portion of the blood vessel;
   the system further comprising:
   a control device adapted to control the hypertension treatment device to heat the wall portion of the renal artery to cause expansion thereof and control the temperature of said heating surface based on the patient's general blood pressure, to:
      increase the temperature for increasing the dilation of said renal artery and thereby control the lowering of the patient's general blood pressure, or
      decrease the temperature for reducing the dilation to thereby control the increasing of the patient's general blood pressure,
   wherein the control device comprises an implantable internal control unit adapted to, in response to signals from a sensor, directly control the hypertension device over time, in accordance with an activity schedule program, and to directly control the constriction device, wherein the sensor is adapted to sense at least the temperature of the heating surface and the general blood pressure of the patient.

2. The system according to claim 1, wherein the temperature of said heating surface is controlled by the internal control unit.

3. The system according to claim 1, further comprising a power supply and electronic circuitry adapted to power the heating surface.

4. The system according to claim 3, wherein said power supply is a rechargeable power supply.

5. The system according to claim 4 further comprising a wireless energy transmitter for wireless charging of the power supply from outside the patient's body.

6. The system according to claim 1, wherein the heating surface comprises an electronic element adapted to cool a second surface.

7. The system according to claim 6, wherein the electronic element is a peltier element.

8. The system according to claim 1, further comprising at least one of the following: at least one push button with a switch implantable in the patient for manually and non-invasively controlling the device, and a wireless remote control for non-invasively controlling the device.

9. The system according to claim 1 further comprising a wireless energy transmitter for non-invasively energizing implantable energy consuming components of the device with wireless energy.

10. The system according to claim 9, further comprising an energy-transforming device for transforming the wireless energy transmitted by the energy transmission transmitter from a first form into a different form of energy, wherein the energy-transforming device is adapted to perform at least one of the following: a) directly power implantable energy consuming components of the device with the different form of energy, and b) with the system further comprising, an implantable source of energy for powering implantable energy consuming components of the device, chargeable by the wireless energy, power the implantable energy source with the different form of energy, as the energy-transforming device transforms the first form of energy transmitted by the energy transmitter into the different form of energy.

11. The system according to claim 1 further comprising a wireless remote control adapted to send a wireless control signal, and wherein the signal comprises a frequency, amplitude, or phase modulated signal or a combination thereof.

12. The system according to claim 1, wherein the control device comprises an external control unit intended to be outside the patient's body.

13. The system according to claim 1, wherein the internal control unit is adapted to be programmable by an external control unit.

14. The system according to claim 1, further comprising an operation device for reversible operating the constriction device, the operation device comprising at least one of:
at least one motor adapted to be operable to perform a reversible function and comprising a servo system designed to transfer a weak force acting on a moving element having a long stroke into a strong force acting on another moving element having a short stroke, and
at least one reservoir adapted to hold hydraulic fluid and wherein the operation device is adapted to distribute hydraulic fluid from the reservoir to expand a cavity in the hydraulic constriction device, and reversibly distribute hydraulic fluid from the cavity to the reservoir.

15. The system according to claim 1, wherein the constriction device is one of a mechanical device and a hydraulic device.

16. The system according to claim 1, wherein the sensor is at least one of: a pressure sensor, a strain sensor, a flow sensor, a spectro-photometrical sensor, and a sensor for sensing the distribution of the stimulation of the blood vessel.

17. The system according to claim 1, wherein the constriction device comprises a contraction element operated by a bellows.

18. The system according to claim 1, wherein the constriction device comprises at least two clamping elements.

19. The system according to claim 18, wherein the clamping elements are slidable back and forth relative to the blood vessel.

20. The system according to claim 18, wherein the clamping elements are spring loaded.

* * * * *